(12) United States Patent
Yamamoto et al.

(10) Patent No.: US 9,462,934 B2
(45) Date of Patent: Oct. 11, 2016

(54) WASHING TREATMENT APPARATUS AND WASH TREATMENT METHOD

(75) Inventors: Hiroaki Yamamoto, Osaka (JP); Kohichi Tamura, Osaka (JP); Keizoh Nariyuki, Osaka (JP); Hiroshi Unemori, Osaka (JP)

(73) Assignee: SHARP KABUSHIKI KAISHA, Osaka (JP)

( * ) Notice: Subject to any disclaimer, the term of this patent is extended or adjusted under 35 U.S.C. 154(b) by 513 days.

(21) Appl. No.: 13/980,489

(22) PCT Filed: Sep. 13, 2011

(86) PCT No.: PCT/JP2011/070822
§ 371 (c)(1),
(2), (4) Date: Jul. 18, 2013

(87) PCT Pub. No.: WO2012/098732
PCT Pub. Date: Jul. 26, 2012

(65) Prior Publication Data
US 2013/0298945 A1 Nov. 14, 2013

(30) Foreign Application Priority Data
Jan. 18, 2011 (JP) .................................. 2011-008302

(51) Int. Cl.
*A61B 1/12* (2006.01)
*A61B 90/70* (2016.01)

(52) U.S. Cl.
CPC .............. *A61B 1/123* (2013.01); *A61B 1/125* (2013.01); *A61B 90/70* (2016.02); *A61B 2090/701* (2016.02)

(58) Field of Classification Search
None
See application file for complete search history.

(56) References Cited

U.S. PATENT DOCUMENTS

| | | | |
|---|---|---|---|
| 5,443,801 A * | 8/1995 | Langford | A61B 1/00059 134/137 |
| 5,554,228 A | 9/1996 | Giordano et al. | |

(Continued)

FOREIGN PATENT DOCUMENTS

| | | |
|---|---|---|
| JP | 2004/504868 A | 2/2004 |
| JP | 2006/06565 | 1/2006 |

(Continued)

OTHER PUBLICATIONS

Notification Concerning Transmittal of International Preliminary Report on Patentability dated Aug. 1, 2013 regarding International Application No. PCT/JP2011/070822.

(Continued)

*Primary Examiner* — Michael Barr
*Assistant Examiner* — Cristi Tate-Sims
(74) *Attorney, Agent, or Firm* — Keating & Bennett, LLP

(57) ABSTRACT

A washing treatment apparatus and a washing treatment method are provided. A washing treatment apparatus washes in a washing container an object to be washed including a tubular portion, and a main body portion to which one end portion of the tubular portion is connected. The washing treatment apparatus includes a washing solution supply unit which pressurizes and supplies a washing solution to the washing container, a penetration hole portion which is provided on the washing container and includes a penetration hole into which the tubular portion can be inserted, an outlet hole portion which is provided on the washing container and includes an outlet hole through which the washing solution supplied into the washing container flows out to adjust pressure of the washing solution in the washing container to predetermined pressure.

6 Claims, 5 Drawing Sheets

(56) References Cited

U.S. PATENT DOCUMENTS

| | | | |
|---|---|---|---|
| 5,892,462 | A | 4/1999 | Tran |
| 5,921,256 | A | 7/1999 | Barin |
| 6,027,572 | A | 2/2000 | Labib et al. |
| 6,408,861 | B1 | 6/2002 | Ortega |
| 6,454,871 | B1 | 9/2002 | Labib et al. |
| 6,485,684 | B1 * | 11/2002 | Mapson ............. A61B 1/00057 206/210 |
| 6,585,943 | B1 * | 7/2003 | Sanford ................ A61B 1/123 134/200 |
| 2001/0047813 | A1 | 12/2001 | Labib et al. |
| 2002/0112743 | A1 | 8/2002 | Tabani et al. |
| 2002/0189647 | A1 | 12/2002 | Labib et al. |
| 2004/0007255 | A1 | 1/2004 | Labib et al. |
| 2005/0028845 | A1 | 2/2005 | Labib et al. |
| 2005/0126599 | A1 | 6/2005 | Labib et al. |
| 2005/0150831 | A1 | 7/2005 | Tabani et al. |
| 2007/0185385 | A1 | 8/2007 | Noguchi et al. |
| 2008/0112846 | A1 | 5/2008 | Dieras et al. |
| 2008/0264454 | A1 | 10/2008 | Tabani et al. |
| 2009/0090398 | A1 * | 4/2009 | Onishi ................... A61B 1/122 134/167 C |
| 2009/0205687 | A1 * | 8/2009 | Onishi ................... B08B 9/032 134/136 |
| 2009/0217956 | A1 * | 9/2009 | Noguchi ................ A61B 1/123 134/57 R |
| 2009/0229632 | A1 | 9/2009 | Labib et al. |
| 2010/0004510 | A1 * | 1/2010 | Kuroshima ........... A61B 1/012 600/158 |

FOREIGN PATENT DOCUMENTS

| | | | | |
|---|---|---|---|---|
| JP | 2009-142324 | * | 2/2009 | ............... A61B 1/12 |
| JP | 2009/142324 | A | 7/2009 | |
| TW | 200635622 | A | 10/2006 | |

OTHER PUBLICATIONS

Notification of Transmittal of Translation of the International Preliminary Report on Patentability dated Aug. 1, 2013 regarding International Application No. PCT/JP2011/070822.

International Search Report dated Oct. 11, 2011 for PCT/JP2011/070822.

* cited by examiner

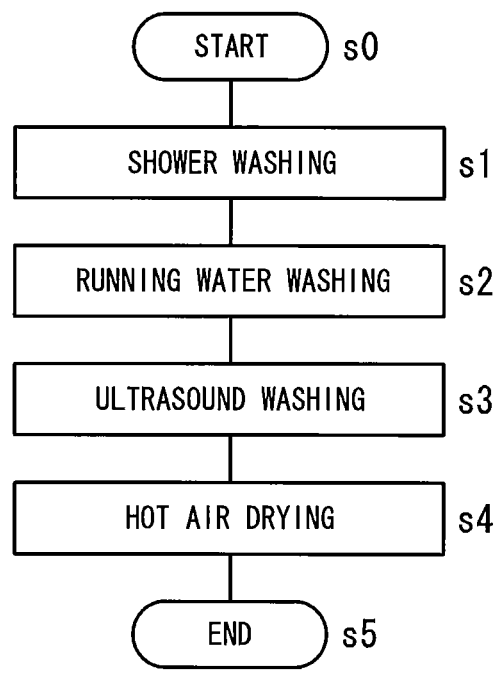

WASHING TREATMENT APPARATUS AND WASH TREATMENT METHOD

TECHNICAL FIELD

The present invention relates to a washing treatment apparatus which includes a tubular portion, and a main body portion to which one end portion of the tubular portion is connected, and performs washing treatment for a subject to be treated such as a medical endoscope or a medical manipulator, for example, with any one of washing, sterilizing, and rinsing, or with combination thereof, and a washing treatment method.

BACKGROUND ART

In recent years, many medical appliances such as an endoscope, a medical manipulator, and the like, which have a tubular portion which is long and thin and a tip end thereof is inserted into a body cavity for observation or an operation, have been developed and used. Since the medical appliances are used by being inserted into a body cavity of a patient, from a hygiene viewpoint for prevention of infection, it is necessary to wash and clean both inside and outside of the medical appliances for them to be clean, by washing treatment such as washing, sterilizing, and rinsing, or with combination thereof, when re-using the medical appliances. However, since the medical appliances have long and thin tubes as those are necessary for functions and usages, a cleaning agent or a disinfectant does not sufficiently pass through the inside of the thin tubes during the washing treatment.

A washing treatment apparatus and a washing treatment method of the related art for such medical appliances having a thin tubular structure are disclosed in Patent Literature 1, for example. The washing treatment apparatus of the related art includes a washing bath in which an endoscope is loaded, a connection tube to which at least a washing solution is supplied, a guide member which guides the connection tube to an axial direction of a channel port of the endoscope provided on an external side of the washing bath, a movement mechanism which moves the connection tube through the guide member, a sealing member for sealing the connection tube and the channel port, and a partition which forms a sealed structure in which the movement mechanism and a part of the connection tube are provided.

CITATION LIST

Patent Literature

Patent Literature 1: Japanese Examined Patent Publication JP-B2 4468747

SUMMARY OF INVENTION

Technical Problem

In such a washing treatment apparatus of the related art, when washing an endoscope, by an external pressure unit, a portion between the outside of a sealed space and a channel port is provided to be in a communicated state to the sealed space formed with a tubular portion of an endoscope and a main body portion connected thereto, so as not to leak a washing solution to the outside of the sealed space, a washing solution and a disinfectant are supplied to the inside of the sealed space, and washing treatment is performed. In this case, if sealability of the sealed space is damaged, washing solutions such as a washing solution, a disinfectant and a rinsing solution are leaked from a portion where sealability is damaged to outside of the sealed space, and if the washing solutions are leaked downstream of the leaking portion described above in a washing solution passing direction, for example, towards the main body portion, flow volume of the washing solution which flows to the tubular portion connected to the main body portion is decreased, and efficiency of washing, sterilizing, and rinsing is degraded.

Even in the case where the sealed space retains sealability, the washing solution is supplied to the inside of the sealed space by pressure of the pressure unit such as a pump, and accordingly, if internal pressure is increased and pressure capacity of the pressure unit reaches the vicinity of the limit, the pressure unit runs idle, and sufficient flow volume for washing and sterilizing cannot be obtained.

For solving such problems, solutions are considered to change the pressure unit to a pressure unit having great supplying capacity of the washing solutions or to extend the washing time, however, with these solutions, the apparatus becomes expensive or processing ability is degraded. In addition, for washing surfaces of the outer side, which is the outside of the sealed space of the main body portion and the tubular portion, a separate configuration for washing the surfaces outside of the main body portion and the tubular portion is necessary, the configuration of the apparatus becomes complicated, and the manufacturing cost increases.

An object of the invention is to provide a washing treatment apparatus and a washing treatment method which can wash the inside and outside of a portion to be washed at low cost, without degrading washing treatment ability.

Solution to Problem

The invention provides a washing treatment apparatus which washes an object to be washed including a tubular portion in which a thin tubular flow path is formed, and a main body portion to which one end portion of the tubular portion is connected and in which a thin tubular flow path is formed, comprising:

a washing container to which a washing solution is supplied, and which includes a penetration hole portion including a penetration hole into which the tubular portion can be inserted, and an outlet hole portion including an outlet hole through which the washing solution supplied into the washing container flows out to adjust pressure of the washing solution in the washing container to predetermined pressure; and a washing solution supply unit which pressurizes and supplies the washing solution to the washing container, the main body portion of the object to be washed being accommodated in the washing container, and the washing solution being passed through a flow path in the tubular portion from a flow path in the main body portion.

In the invention, it is preferable that the outlet hole is formed between the penetration hole portion, and the tubular portion inserted into the penetration hole portion.

In the invention, it is preferable that the washing treatment apparatus includes a plug which is detachably inserted in the penetration hole portion of the washing container and closes the penetration hole in a liquid-tight manner.

In the invention, it is preferable that the washing treatment apparatus includes a water discharging unit which accommodates the washing container, and collects and discharges a washing solution which has been used for washing of the washing container and/or the object to be washed.

In the invention, it is preferable that the washing treatment apparatus includes a gas supply unit which supplies gas into the washing container.

The invention provides a washing treatment method, comprising:

accommodating at least a main body portion of an object to be washed which includes a tubular portion and the main body portion to which one end portion of the tubular portion is connected, in which a thin tubular flow path is formed inside of the tubular portion and the main body portion, in a washing container, putting a washing solution in the washing container through the flow path in the tubular portion from the flow path in the main body portion, in a state where the tubular portion is protruded to an outside from the washing container through a penetration hole provided on the washing container, and washing the object to be washed; and causing the washing solution pressurized and supplied into the washing container to flow out through an outlet hole provided on the washing container to adjust pressure of the washing solution in the washing container to predetermined pressure.

In the invention, it is preferable that the predetermined pressure is set to be close to supplying pressure of the washing solution to be supplied into the washing container.

In the invention, it is preferable that a plurality of penetration holes is provided on the washing container, and the plurality of penetration holes are selectively opened and closed by a plug according to presence or absence of a tool to be washed, to adjust flow volume of the washing solution.

In the invention, it is preferable that gas is supplied to washed object, to dry the washed object.

Advantageous Effects of Invention

According to the present invention, the penetration hole portion and the outlet hole portion are provided on the washing container. The main body portion and a part of the tubular portion, one end portion of which is connected to the main body portion, are accommodated in the washing container. If the washing solution is supplied into the washing container and the washing container is filled with the washing solution, the washing solution in the washing container is introduced to the flow path in the tubular portion through the flow path in the main body portion, and discharged from a tip of the tubular portion to the outside, and the inside of the flow path which forms thin tubes in the main body portion and the tubular portion is washed, sterilized, and rinsed. Since the outlet hole portion is provided on the washing container, the washing solution in the washing container flows out through the outlet hole of the outlet hole portion, and the pressure of the washing solution in the washing container is adjusted to the predetermined pressure. By setting the predetermined pressure to be the supplying pressure of the washing solution supply unit or to be close thereto, with such predetermined pressure, excessive load is not applied to the washing solution supply unit, the washing solution passes through the flow path in the main body portion and the flow path in the tubular portion, the flow path in the main body portion and the flow path in the tubular portion are washed, sterilized, and rinsed by the washing solution, and the surface of the outer side of the main body portion in the washing container and the surface of the outer side of a part of the tubular portion in the washing container can be subjected to washing treatment at the same time by the washing solution in the washing container. Accordingly, the inside and outside of the object to be washed can be washed at low cost without degrading washing treatment ability.

According to the present invention, the flow path in the main body portion and the flow path of the tubular portion can be washed, sterilized, and rinsed by the washing solution, and the surface of the outer side of the tubular portion can be subjected to the washing treatment at the same time by the liquid flows out through the outlet hole to the washing container.

According to the invention, since the plug which can be detachably inserted in the penetration hole portion is provided, the penetration hole of the penetration hole portion which is opened when the tubular portion of the object to be washed is not mounted, can be closed by the plug, and even in a case where the number of the installed objects to be washed is smaller than the number of the objects to be washed capable of being installed in the washing container, the opening area of the penetration hole portion can be decreased, and the flow volume leaking out from the washing container to the outside of the washing container can be decreased.

According to the invention, by the water discharging unit, the washing container can be accommodated, and a washing solution which has been used for washing of the washing container and/or the object to be washed can be collected and discharged.

In the invention, since the gas can be supplied into the washing container by the gas supply unit, drying of the washing container and the object to be washed after the washing can be facilitated.

Other and further objects, features, and advantages of the invention will be more explicit from the following detailed description taken with reference to the drawings.

BRIEF DESCRIPTION OF DRAWINGS

FIG. 5 is a flowchart for illustrating washing treatment procedure of the objects to be washed by the washing treatment equipment.

DESCRIPTION OF EMBODIMENTS

Figure 1:
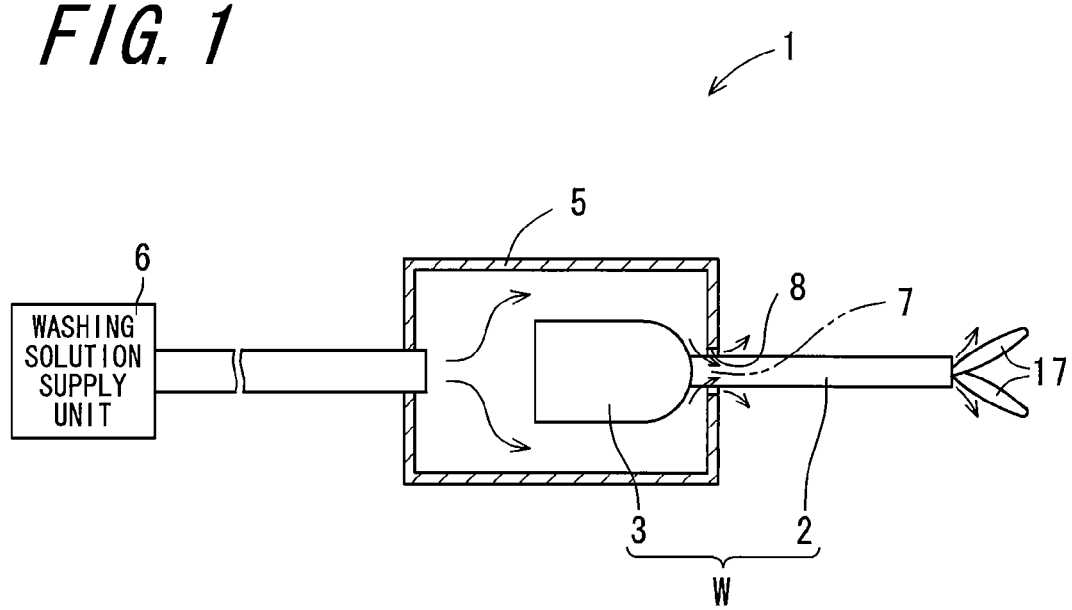
FIG. 1 is a cross-sectional view schematically showing a washing treatment apparatus according to one embodiment of the invention seen from the top.

Now referring to the drawings, preferred embodiments of the invention are described below.

Figure 2:
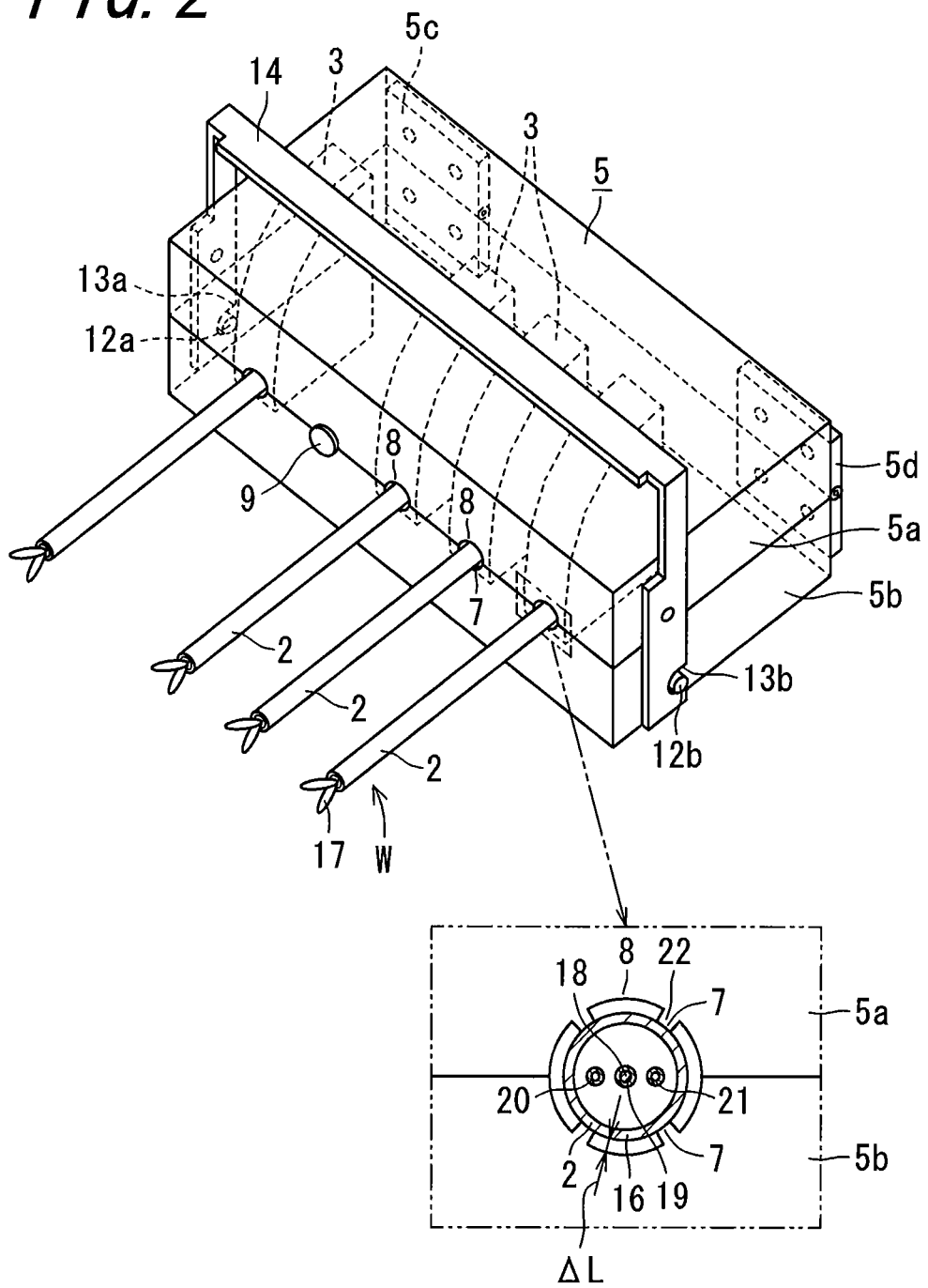
FIG. 2 is a perspective view showing a state where a plurality of objects to be washed are accommodated in a washing container.

FIG. 1 is a cross-sectional view schematically showing a washing treatment apparatus 1 according to one embodiment of the invention seen from the top, and FIG. 2 is a perspective view showing a state where a plurality of objects to be washed W are accommodated in a washing container 5. The washing treatment apparatus 1 of the embodiment is used for executing a washing treatment method according to the invention. This washing treatment apparatus 1 washes the objects to be washed W in the washing container 5. The object to be washed W includes a tubular portion 2 and a main body portion 3 to which one end portion of the tubular portion 2 is connected, and a thin tubular flow path is formed inside of the tubular portion 2 and the main body portion 3. In the washing treatment apparatus 1, in a state where the main body portion 3 is accommodated in the washing container 5 and the tubular portion 2 is protruded outside from the washing container 5, a washing solution in the washing container 5 passes through the flow path in the tubular portion 2 from the flow path in the main body portion 3, and thus, the objects to be washed W can be washed.

As an example, the tubular portion 2 has a structure in which a tube made from polytetrafluoroethylene having an outer diameter of about 2.2 mm, an inner diameter of about 1.6 mm, and a length of about 430 mm, which introduces fluid such as a medicinal solution used for washing of affected parts to a tip end, is inserted into an outer tube made of resin having an outer diameter of about 8.4 mm, an inner diameter of 6.8 mm, and a length of about 450 mm, and a thin tube is formed by a passage in the tube and a space between the tube and the other insertion equipment.

The washing treatment apparatus 1 includes a washing solution supply unit 6 which pressurizes and supplies the washing solution to the washing container 5, a penetration hole portion 7 which is provided on the washing container 5 and includes a penetration hole into which the tubular portion 2 can be inserted, an outlet hole portion 8 which is provided on the washing container 5, and includes an outlet hole through which the washing solution supplied into the washing container 5 flows out to adjust pressure of the washing solution in the washing container 5 to predetermined pressure, a plug 9 which is detachably inserted in the penetration hole portion 7 of the washing container 5 and liquid-tightly closes the penetration hole, a water discharging unit 10 (see FIG. 4 which will be described later) which accommodates the washing container 5, and collects and discharges a washing solution which has been used for washing of the washing container 5 and/or the objects to be washed W, and a gas supply unit 11 (see FIG. 4 which will be described later) which supplies gas for drying into the washing container 5.

The outlet hole of the outlet hole portion 8 is realized by a cylindrical space formed between the penetration hole portion 7 and an outer periphery surface of the tubular portion 2 inserted into the penetration hole portion 7. The object to be washed W is a medical endoscope in the embodiment, however, in the other embodiment of the invention, the object to be washed W may be a medical manipulator. To describe the structure of the tubular portion 2 as an example, a guide tube 19 to which a driving wire 18 which drives a scalpel for section 17 provided on a tip end portion is inserted, and a plurality of tubes 20 and 21 which introduces fluid such as a normal saline solution, a medicinal solution, or medical gas to the tip end portion are inserted into a vertical cylindrical outer tube 16 for medicinal solution made of stainless steel or synthesis resins. The guide tube 19 and the plurality of tubes 20 and 21 are disposed across from a base end portion which is one end portion of the outer tube 16 to the main body portion 3, and the thin tubular flow path is formed in the tubular portion 2 and the main body portion 3.

The penetration hole portion 7 is formed by a pair of cut portions each of which is formed in a semicircular shape having a radius substantially equal to a radius of the tubular portion 2 on the other side wall portion of each container portions 5a and 5b on a long side, when seen from the front, and the outlet hole portion 8 is formed by expanding the radius thereof by a width ΔL in a radius line direction, outwards in a radius direction with respect to the penetration hole portion 7. This width ΔL is selected to be 0.5 mm, for example. Such an outlet hole portion 8 is evenly divided by a plurality of (in the embodiment, four) protrusions 22 defining the penetration hole portion 7, in a circumferential direction, and the outlet hole portion 8 which defines the outlet hole is formed between each of the protrusions 22.

In a state of inserting the tubular portion 2 of the object to be washed W into the penetration hole portion 7, each protrusion 22 is positioned so as to support the outer periphery surface of the tubular portion 2, and the outlet hole through which the washing solution flows out is formed between the outer periphery surface of the tubular portion 2 and the outlet hole portion 8.

Such an outlet hole functions as an orifice, and the washing solution which flows out through the outlet hole practically forms cylindrical discharging fluid immediately after discharging, comes in contact with the outer surface of the tubular portion 2, can wash the outer surface of the tubular portion 2, and can adjust liquid pressure inside the washing container 5, so that the pressure of the washing solution supplied from the washing solution supply unit 6 into the washing container 5 becomes the predetermined pressure, for example, 150 to 200 kPa. Accordingly, as described in the related art, excessive load is not applied to the washing solution supply unit 6, the pump or the like is prevented from running idle, and the inside of the objects to be washed W can be smoothly washed.

In addition, by supplying the washing solution to the washing container 5 by the washing solution supply unit 6, at least one process of washing, sterilizing, and rinsing is performed with respect to the tubular portion 2 and the inside and outside of the main body portion 3 in the washing container 5 and the inside of the tubular portion 2. Also, by the washing solution flowed out from a space intentionally provided between the outlet hole portion 8 provided on the washing container 5 and the outer periphery surface of the tubular portion 2, to the outside of the washing container 5, the outer tube side of the tubular portion 2 can be washed, sterilized, or rinsed at the same time. The washing solution supply unit 6 may be realized by a constant-pressure pump.

The washing container 5 includes a box-shaped upper container portion 5a which forms a rectangular parallelepiped, a box-shaped lower container portion 5b which forms a rectangular parallelepiped, a pair of hinge pieces 5c and 5d which rotatably connect one side wall portion of the upper container portion 5a on a long side and one side wall portion of the lower container portion 5b on a long side, around an axis parallel with the long side direction, a manipulation lever 14 which is rotatably provided on both side wall portions of the upper container portion 5a on a short side, around an axis parallel with the long side direction, and locking pins 12a and 12b each of which is provided so as to be protruded to both side wall portions of the lower container portion 5b on a short side.

Recesses 13a and 13b to which each of the locking pins 12a and 12b is fit in an inserted manner, are provided on each free end portion of the manipulation lever 14, respectively, each of the container portions 5a and 5b is prevented from opening by fitting the locking pins 12a and 12b to the recesses 13a and 13b. In a case of opening each of the container portions 5a and 5b, by manipulating the manipulation lever 14 for angular displacement of the locking pins 12a and 12b from the recesses 13a and 13b in a separating direction, a locked state of the upper container portion 5a with respect to the lower container portion 5b is released, each of the container portions 5a and 5b is opened, and thus, one or a plurality of objects to be washed W can be accommodated in the container 5, and the accommodated objects to be washed W can be taken out of the washing container 5. Such a washing container 5 may be made of stainless steel having high chemical resistance and oxidation resistance, or may be made of fluorine resins.

Figure 3:
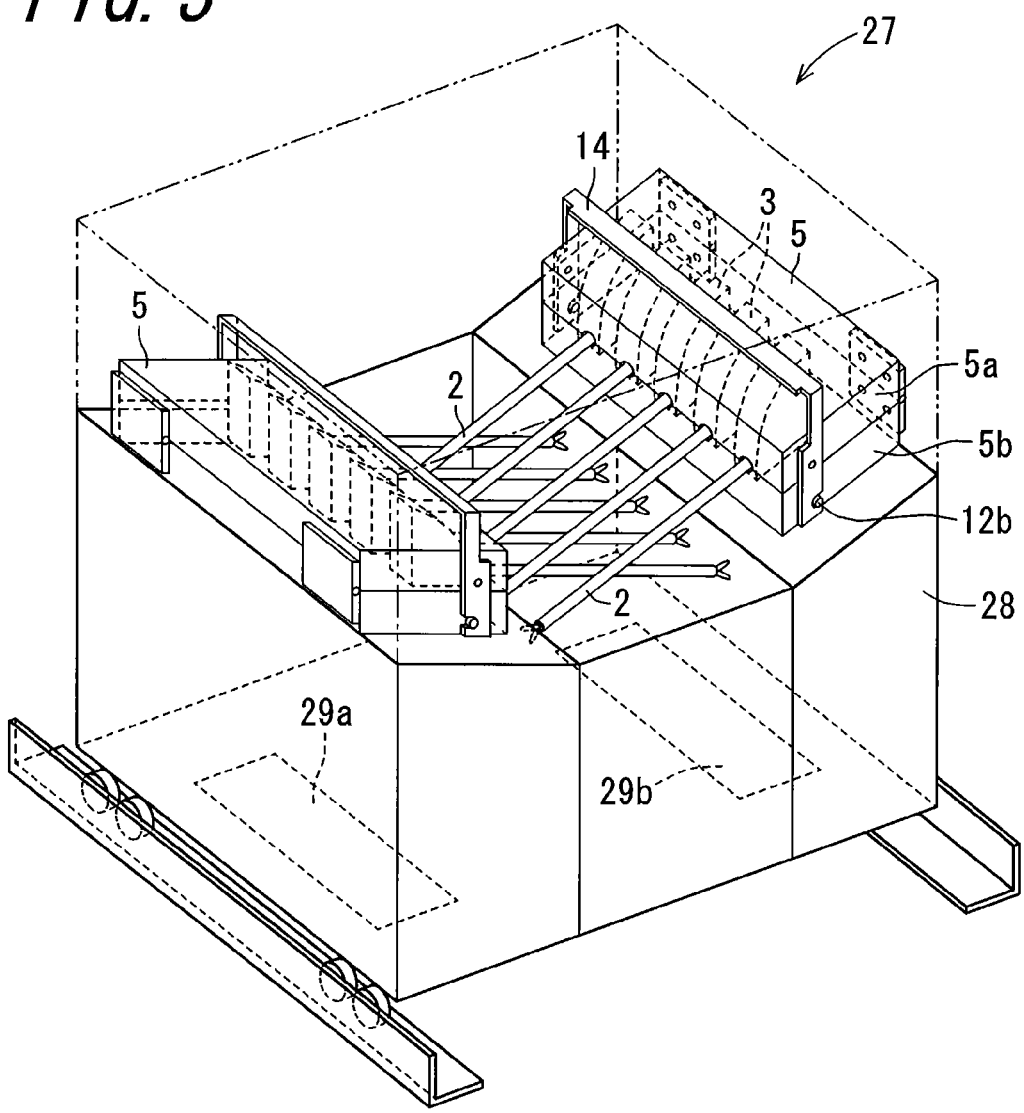
FIG. 3 is a perspective view showing washing treatment equipment on which the washing treatment apparatus is mounted.
Figure 4:
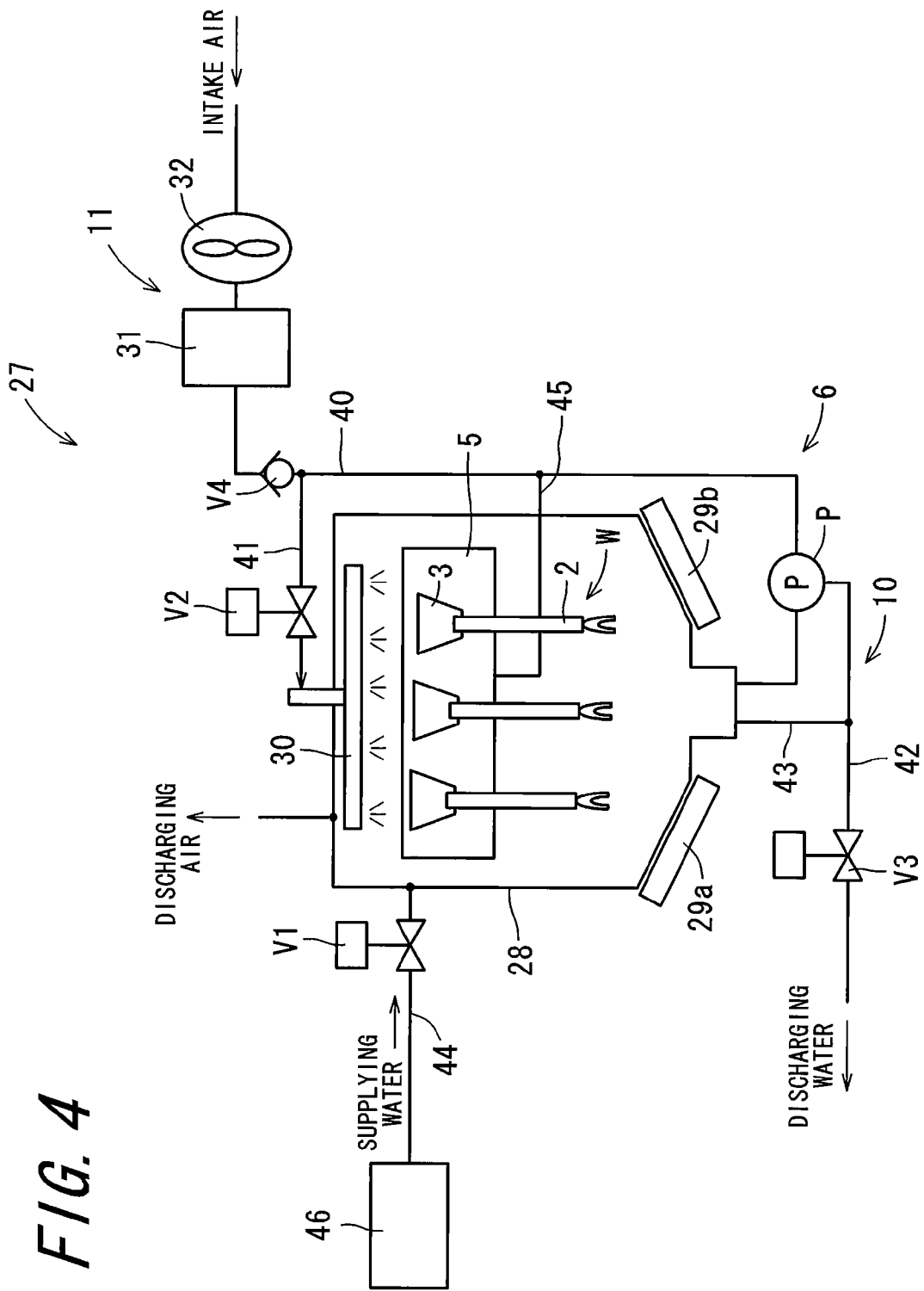
FIG. 4 is a system diagram of the washing treatment equipment.

FIG. 3 is a perspective view showing washing treatment equipment 27 on which the washing treatment apparatus 1 is mounted, and FIG. 4 is a system diagram of the washing treatment equipment 27. The washing treatment equipment 27 includes a washing bath 28 on which a plurality of (in the embodiment, two) washing containers 5 each accommodating the plurality of objects to be washed W are loaded, a pair of ultrasound vibration panels 29a and 29b which are provided on a bottom portion of the washing bath 28, a water supply valve V1, a rotation nozzle head 30 which ejects the washing solution while being rotated around the vertical axis, a rotation nozzle head valve V2, a solution sending pump P, a water discharging valve V3, a check valve V4, a heating apparatus 31, and a blower 32.

In each of the washing container 5, the tubular portion 2 of the object to be washed W is inserted into the penetration hole portion 7, and the main body portion 3 is accommodated in the washing container 5. In a state where the plurality of objects to be washed W are accommodated in the washing container 5, tubular portions 2 are disposed in parallel with each other to be protruded from the washing container 5, and the tip end portion of the tubular portion 2 and the vicinity thereof are inserted into the washing bath 28 from the opening of the upper portion of the washing bath 28, and are immersed in the washing solution stored in the washing bath 28.

The bottom portion of the washing bath 28 and an outlet hole portion of heated air as air for drying of the heating apparatus 31 are connected to each other by a first piping 40. The check valve V4 and the solution sending pump P are provided on the first piping 40. In addition, a sixth piping 45 is branched from the first piping 41, and is connected to the washing container 5. One end portion of a second piping 41 is connected to a portion between the check valve V4 and the solution sending pump P of the first piping 40, and the other end portion of the second piping 41 is connected to an input port of the rotation nozzle head 30. The rotation nozzle head valve V2 is provided on the second piping 41.

A third piping 42 is connected to the solution sending pump P, and the water discharging valve V3 is provided on the third piping 42. One end portion of a fourth piping 43 is connected to a portion between the water discharging valve V3 and the solution sending pump P of the third piping 42, and the other end portion of the fourth piping 43 is connected to the bottom portion of the washing bath 28. If the solution sending pump P is driven in a state of closing the water discharging valve V3 and opening the rotation nozzle head valve V2, the washing solution in the washing bath 28 is supplied to the rotation nozzle head 30 through the first piping 40 and the second piping 41, and the inside of the washing bath 28 can be washed with a shower.

A fifth piping 44 on which the water supply valve V1 is provided is connected to the upper portion of the washing bath 28 on a side wall, and by opening the water supply valve V1, the washing solution such as clean washing water which is sterilized and filtered from a washing solution generation unit 46 can be supplied into the washing bath 28. In the embodiment, the washing solution supply unit 6 includes the washing solution generation unit 46, the water supply valve V1, the washing bath 28, the solution sending pump P, the first piping 40, and the sixth piping 45. The water discharging unit 10 includes the washing bath 28, the third piping 42, the fourth piping 43, and the water discharging valve V3. The gas supply unit 11 includes the heating apparatus 31, the blower 32, the check valve V4, the first piping 40, and the sixth piping 45.

For checking a flowing state of the washing solution for the objects to be washed W by presence and absence of the outlet hole portion 8 of the washing container 5, the inventors measured solution volume at the time when the washing solution supplied to the washing container 5 was flowed out to the outside through the flow path in the tubular portion 2 of the objects to be washed W by the solution sending pump P in the washing treatment equipment 27. In this experiment, a medical manipulator is used as the object to be washed W, the main body portion 3 is a driving unit of the manipulator, and the tubular portion 2 is a jig unit such as a scalpel for section 17. A volute stainless pump is used as the solution sending pump P, and a supplied amount of the washing solution to the washing container 5 is adjusted by an input value of an inverter. The experimental results are shown in Table 1.

TABLE 1

| Condition of pressurization pump | | (A) No leaking flow path from washing container | | | (B) Leaking flow path from washing container | | |
|---|---|---|---|---|---|---|---|
| | | Total flow | Flow volume | Flow volume | Total flow | Flow volume | Flow volume |
| Controlling frequency of pump [Hz] | Pressing pressure of pump [kPa] | volume discharged from pump [cc/min] | discharged from tip end [cc/min] | leaking from base [cc/min] | volume discharged from pump [cc/min] | discharged from tip end [cc/min] | leaking from base [cc/min] |
| 60 | 240 | 150 | 150 | 0 | 600 | 250 | 350 |
| 50 | 160 | 150 | 150 | 0 | 450 | 200 | 250 |
| 40 | 100 | 150 | 150 | 0 | 420 | 120 | 300 |

As clear from Table 1, in a case with no outlet hole portion 8 on the washing container 5, even when the pressing pressure of the solution sending pump P which is a pressurization unit of the washing solution supply unit 6 is increased, the flow volume of the liquid discharged from the tip end of the tubular portion 2 does not change. At that time, it is easily expected that the solution sending pump sends the liquid while running idle.

On the other hand, in a case where the outlet hole portion 8 is provided on the washing container 5, the discharging flow volume of the liquid discharged from the tip end of the tubular portion is increased according to the increase of the pressing pressure of the solution sending pump P, and when the pressing pressure of the pump is 240 kPa, the discharging flow volume from the tip end of the tubular portion 2 becomes about double, compared to the case without the outlet hole portion 8. In addition, the flow volume of the liquid flowing to the outside of the tube from the base of the tubular portion 2 is also increased according to the increase of the pressing pressure of the solution sending pump P.

Accordingly, the flow path of the tubular portion 2 on the inner side, and the outside thereof are washed at the same time, and it is found that the flow path on the inner side is washed with the washing solution having flow volume greater than that of the case without the outlet hole portion 8 on the washing container 5.

To wash the surface of the tubular portion 2 on the outer side, FIG. 2 described above shows an example of the washing container 5 in which the outlet hole portion 8 having a larger diameter than that of the penetration hole portion 7 is provided concentrically with the penetration hole portion 7 of the washing container 5. Compared to the maximum number of the objects to be washed W which can be set in the washing container 5, in a case where the objects to be washed W as the washing targets are insufficient, by inserting the plug 9 in the penetration hole portion 7 on a portion where the objects to be washed W are not set, the flow path cross-sectional area corresponding to the opening area of the penetration hole portion 7 can be decreased, and the liquid volume of the washing solution to be leaked from the washing container 5 to the outside of the washing container 5 can be decreased.

In the other embodiment of the invention, a washing container can be set which has the same configuration as the washing container 5 shown in FIG. 2 and can accommodate only one object to be washed W, and one of a plurality of this washing container can be connected to each other, if necessary. In any cases, the outlet hole portion 8 is provided as a flow path for intentionally leaking the washing solution to a part of the washing container 5, and the inside and outside of the tubular portions 2 of the objects to be washed W mounted on the washing container 5 can be washed at the same time.

FIG. 5 is a flowchart for illustrating washing treatment procedure of the objects to be washed W by the washing treatment equipment 27. The washing treatment using both ultrasound and shower will be described with reference to FIGS. 1 to 4. The washing treatment equipment 27 is configured so as to selectively switch and set a ultrasound washing mode by ultrasound provided from the ultrasound vibration panels 29a and 29b, and a shower washing mode for performing washing by washing solution shower ejected from the rotation nozzle head 30 which rotates in the washing bath 28.

First, in Step s0, the washing treatment operation is started and in Step s1, a shower washing step is started. In this shower washing step, after the water supply valve V1 is opened and water is supplied to the washing bath 28, the water supply valve V1 is closed, the rotation nozzle head valve V2 is opened, the water is sent to the rotation nozzle head 30 disposed on a ceiling portion in the washing bath 28 by the pump P, and after the shower washing of the entire of the inside of the bath, the pump P is stopped, the water discharging valve V3 is opened, and water discharging is performed.

Next, the process proceeds to a running water washing step of Step s2 from Step s1. In the running water washing step, in the same manner as Step s1 described above, after water supply into the washing bath 28, the water supply valve V1 is closed, the pump P is driven, the water is sent to the objects to be washed W in the washing container 5, and the objects to be washed W having flow paths forming thin tubes set in the washing container 5 are washed.

In the shower washing step or the running water washing step, the water supply valve V1 may be opened and closed to supply water into the washing bath 28 if necessary, and a cleaning agent or a disinfectant may be added into the bath from a cleaning agent input port (not shown) provided on the washing bath 28, if necessary.

Then, if the process proceeds to a ultrasound washing step of Step s3, after the water supply valve V1 is opened and closed to supply water until the contaminated tip end portion of the objects to be washed W in the washing bath 28 is immersed in the washing solution, and the ultrasound washing is performed by operating the ultrasound vibration panels 29a and 29b provided on the bottom portion of the washing bath 28, the water discharging valve V3 is opened, and the liquid in the washing bath 28 is discharged. In addition, if necessary, the shower washing, and the running water washing from the washing container 5 are performed with only water, and rinsing is performed with a cleaning agent or a disinfectant.

Next, the process proceeds to a hot air drying step of Step s4. After the water in the washing bath 28 is discharged, the heating apparatus 31 and the blower 32 are operated to send hot air into the washing bath 28 and the washing container 5, the inside of the washing bath 28 and the objects to be washed W are dried, and the washing treatment operation ends in Step s5.

According to such a configuration described above, a tool including the tubular portion 2 and including the main body portion 3 connected to the tubular portion 2, that is, the object to be washed W such as a medical endoscope or a medical manipulator is washed, sterilized, or rinsed, or in combination thereof, can be subjected to the washing treatment. The washing solution used for washing, sterilizing, and rinsing, is supplied to the washing container 5 having a sealed structure, the outlet hole portion 8 is provided as an opening separated from the penetration hole portion 7 into which the tubular portion 2 is inserted, the main body portion 3 of the object to be washed W is installed in the washing container 5, the tubular portion 2 is provided on the penetration hole portion 7, and the washing solution is supplied to the washing container 5, and accordingly, the washing treatment apparatus 1 can wash and sterilize the main body portion 3 in the washing container 5 and a part of the tubular portion connected thereto, and can wash and sterilize the surface of the outer side of the tubular portion 2 at the same time, by the washing solution flowed out from the outlet hole of the outlet hole portion 8 provided on the washing container 5 to the outside of the washing container 5.

In addition, by using a gas dissolution washing solution containing microscopic bubbles as the washing solution, physical liquid flow occurs, and the washing solution also easily flows into a narrow portion such as a minute hole or groove on the surface of the object to be washed W, with the decrease of friction resistance due to microscopic bubbles, and thus, detergency can be improved.

In addition, by performing the ultrasound washing as described above, the microscopic bubbles in the washing solution flowed into the narrow portion of the object to be washed W are broken due to cavitation, significant liquid flow locally occurs, and thus, it is possible to perform the washing in more excellent manner.

Further, since the ultrasound comes from the ultrasound vibration panels 29a and 29b and can break the microscopic bubbles in the washing solution in the washing bath 28, it is possible to prevent the minute bubbles in the washing solution from being aggregated to be large bubbles, and it is possible to continuously maintain high detergency.

By performing the ultrasound washing step described above under the reduced pressure, bubbles remaining on the holes on the object to be washed W can be removed, washing solution can flow therein, dissolved air in the washing solution is removed, sound pressure at the time of occurrence of cavitation becomes large, and detergency becomes high than that in a atmosphere pressure state, and thus, more powerful washing can be performed.

Other than performing the step of performing circulation washing by the washing solution containing microscopic bubbles described above for predetermined time and a step of performing the ultrasound washing thereof for predetermined time, by one cycle in the total washing time, by reducing the time of one cycle and repeating a plurality of cycles of the steps, it is possible to prevent the microscopic bubbles in the washing solution from being aggregated to become large, and accordingly, fluidity and displacement efficiency of the washing solution become excellent and higher detergency can be acquired.

Since the washing container 5 which can be sealed by collecting and accommodating the plurality of objects to be washed W, in a case of performing circulation washing with the gas dissolution solution or liquid containing microscopic bubbles, the washing solution containing microscopic bubbles obtained by reducing friction resistance due to microscopic bubbles flows into and circulates the sealed washing container 5 in which the plurality of objects to be washed W are set, and accordingly, the washing solution easily flows into the objects to be washed W and physical liquid flow can occur. Thus, it is possible to efficiently wash the inside of the objects to be washed W.

In the embodiment described above, the outlet hole portion 8 is formed on a position surrounding the penetration hole portion 7, however, in the other embodiment of the invention, the outlet hole portion may be formed on a position separated from the penetration hole portion 7. In addition, the outlet hole portion 8 may be realized by providing a pressure control valve or a component configuring an orifice on the washing container 5.

The invention is not limited to the embodiments described above, and various modifications and alterations are possible without departing the scope of the invention.

The invention may be embodied in other specific forms without departing from the gist or essential characteristics thereof. The present embodiments are therefore to be considered in all respects as illustrative and not restrictive, the scope of the invention being indicated by the appended claims rather than by the foregoing description and all changes which come within the meaning and the range of equivalency of the claims are therefore intended to be embraced therein.

REFERENCE SIGNS LIST

1: Washing treatment apparatus
2: Tubular portion
3: Main body portion
5: Washing container
5a: Upper container portion
5b: Lower container portion
6: Washing solution supply unit
7: Penetration hole portion
8: Outlet hole portion
9: Plug
10: Water discharging unit
11: Gas supply unit
16: Outer tube
17: Scalpel for section
18: Driving wire
19: Guide tube
20, 21: Tube
22: Protrusion
27: Washing treatment equipment
28: Washing bath
29a, 29b: Ultrasound vibration panel
30: Rotation nozzle head
31: Heating apparatus
32: Blower
P: Solution sending pump
V1: Water supply valve
V2: Rotation nozzle head valve
V3: Water discharging valve
V4: Check valve
W: Object to be washed

The invention claimed is:

1. A washing treatment apparatus which washes an object to be washed including a tubular portion in which a thin tubular flow path is formed, and a main body portion to which one end portion of the tubular portion is connected and in which a thin tubular flow path is formed, comprising:
   a washing container to which a washing solution is supplied, and which includes a penetration hole portion including a penetration hole into which the tubular portion can be inserted, and an outlet hole portion including an outlet hole through which the washing solution supplied into the washing container flows out to adjust pressure of the washing solution in the washing container to predetermined pressure; and
   a washing solution supply unit which pressurizes and supplies the washing solution to the washing container,
   the main body portion of the object to be washed being accommodated in the washing container, and
   the washing solution being passed through a flow path in the tubular portion from a flow path in the main body portion, wherein
   the penetration hole portion includes a plurality of protrusions, and
   the outlet hole portion is divided by the plurality of protrusions.

2. The washing treatment apparatus according to claim 1, wherein the outlet hole is formed between the penetration hole portion and the tubular portion inserted into the penetration hole portion.

3. The washing treatment apparatus according to claim 1, further comprising a plug which is detachably inserted in the penetration hole portion of the washing container and closes the penetration hole in a liquid-tight manner.

4. The washing treatment apparatus according to claim 1, further comprising a water discharging unit which accommodates the washing container, and collects and discharges a washing solution which has been used for washing of the washing container and/or the object to be washed.

5. The washing treatment apparatus according to claim 1, further comprising a gas supply unit which supplies gas into the washing container.

6. The washing treatment apparatus according to claim 1, wherein the outlet hole portion is evenly divided by the plurality of protrusions.

* * * * *